United States Patent
Helm et al.

(10) Patent No.: US 11,756,242 B2
(45) Date of Patent: *Sep. 12, 2023

(54) SYSTEM AND METHOD FOR ARTIFACT REDUCTION IN AN IMAGE

(71) Applicants: Medtronic Navigation, Inc., Louisville, CO (US); The Johns Hopkins University, Baltimore, MD (US)

(72) Inventors: Patrick A. Helm, Milton, MA (US); Jeffrey H. Siewerdsen, Baltimore, MD (US); Ali Uneri, Baltimore, MD (US); Wojciech Zbijewski, Baltimore, MD (US); Xiaoxuan Zhang, Baltimore, MD (US); Joseph W. Stayman, IV, Baltimore, MD (US)

(73) Assignee: Medtronic Navigation, Inc., Lafayette, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 17/493,208

(22) Filed: Oct. 4, 2021

(65) Prior Publication Data
US 2022/0028131 A1  Jan. 27, 2022

Related U.S. Application Data

(63) Continuation of application No. 16/375,292, filed on Apr. 4, 2019, now Pat. No. 11,138,768.
(Continued)

(51) Int. Cl.
G06T 11/00     (2006.01)
G06T 5/00      (2006.01)
(Continued)

(52) U.S. Cl.
CPC .......... *G06T 11/006* (2013.01); *A61B 6/5282* (2013.01); *A61B 34/10* (2016.02);
(Continued)

(58) Field of Classification Search
CPC ...... A61B 3090/376; A61B 3090/3764; A61B 34/10; A61B 90/37; A61B 6/5282;
(Continued)

(56) References Cited

U.S. PATENT DOCUMENTS

| | | |
|---|---|---|
| 5,214,686 A | 5/1993 | Webber |
| 9,098,896 B2 | 8/2015 | Barth et al. |

(Continued)

FOREIGN PATENT DOCUMENTS

| | | |
|---|---|---|
| DE | 102015208929 B3 | 6/2016 |
| JP | 2011508620 A | 3/2011 |
| JP | 2017664 A | 1/2017 |

OTHER PUBLICATIONS

European Office Action regarding Patent Application No. 197188840, dated May 10, 2022.
(Continued)

*Primary Examiner* — Daniel G Mariam
(74) *Attorney, Agent, or Firm* — Harness, Dickey & Pierce, P.L.C.

(57) ABSTRACT

Selected artifacts, which may be based on distortions or selected attenuation features, may be reduced or removed from a reconstructed image. Various artifacts may occur due to the presence of a metal object in a field of view. The metal object may be identified and removed from a data that is used to generate a reconstruction.

20 Claims, 6 Drawing Sheets

Related U.S. Application Data

(60) Provisional application No. 62/654,038, filed on Apr. 6, 2018.

(51) Int. Cl.
  *G06T 7/60* (2017.01)
  *A61B 6/00* (2006.01)
  *A61B 34/10* (2016.01)
  *A61B 90/00* (2016.01)

(52) U.S. Cl.
  CPC .............. *A61B 90/37* (2016.02); *G06T 5/002* (2013.01); *G06T 5/005* (2013.01); *G06T 7/60* (2013.01); *A61B 2034/102* (2016.02); *A61B 2090/376* (2016.02); *A61B 2090/3764* (2016.02); *G06T 2207/10124* (2013.01); *G06T 2207/20081* (2013.01); *G06T 2207/20182* (2013.01); *G06T 2207/20221* (2013.01); *G06T 2207/30052* (2013.01)

(58) Field of Classification Search
  CPC . A61B 2034/102; G06T 11/006; G06T 5/002; G06T 5/005; G06T 2207/10024; G06T 2207/10124; G06T 2207/20081; G06T 2207/20221; G06T 2207/30052; G06T 7/60
  USPC ......................................................... 382/128
  See application file for complete search history.

(56) References Cited

U.S. PATENT DOCUMENTS

| | | |
|---|---|---|
| 2003/0181809 A1 | 9/2003 | Hall et al. |
| 2012/0289826 A1 | 11/2012 | Graumann et al. |
| 2013/0070991 A1 | 3/2013 | Yang et al. |
| 2014/0334709 A1 | 11/2014 | Siewerdsen et al. |
| 2015/0178917 A1 | 6/2015 | Yang et al. |
| 2016/0324499 A1 | 11/2016 | Sen Sharma et al. |
| 2017/0165008 A1 | 6/2017 | Finley |
| 2017/0231713 A1 | 8/2017 | Siewerdsen et al. |
| 2018/0070902 A1 | 3/2018 | Lin et al. |
| 2018/0250076 A1 | 9/2018 | Gemmel et al. |
| 2019/0384986 A1 | 12/2019 | Chen et al. |

OTHER PUBLICATIONS

Xu S et al, "Polyenergetic known-component CT reconstruction with unknown material compositions and unknown x-ray spectra", Physics in Medicine and Biology, Institute of Physics Publishing, Bristol GB, Mar. 28, 2017 (Mar. 28, 2017), vol. 62, No. 8, p. 3352-3374.
A Uneri et al, "3D-2D Known-Component Registration for Metal Artifact Reduction in Cone-Beam CT", The 5th International Conference on Image Formation in X-Ray Computed Tomography, May 20, 2018 (May 20, 2018), p. 151-155.
Ha Sungsoo et al, "Metal artifact reduction in CT via ray profile correction", Progress in Biomedical Optics and Imaging, SPIE—International Society for Optical Engineering, Bellingham, WA, US, vol. 9783, Mar. 31, 2016 (Mar. 31, 2016), p. 978334-978334.
Stayman J W et al, "Model-Based Tomographic Reconstruction of Objects Containing Known Components", IEEE Transactions on Medical Imaging, IEEE Service Center, Piscataway, NJ, US, vol. 31, No. 10, Oct. 2012 (Oct. 2012), p. 1837-1848.
International Search Report and Written Opinion dated Jul. 26, 2019 in corresponding/related International Application No. PCT/US2019/026014.
Invitation to Pay Additional Fees dated Jul. 17, 2020 in corresponding/related International Application No. PCT/US2020/026124.
Uneri, et al: "Known-component 3D-2D registration for quality assurance of spine surgery pedicle screw place", Physics in Medicine and Biology, Institute of Physics Publishing, Bristol GB, vol. 60, No. 20, Sep. 30, 2015, pp. 8007-8024, XP020289896, ISSN: 0031-9155, DOI: 10.1088/0031-9155/60/20/8007 [retrieved on Sep. 30, 2015].
Newell, et al: "An intraoperative fluoroscopic method to accurately measure the post-implantation position of pedicle screws", International Journal of Computer Assisted Radiology and Surgery, Springer, DE, vol. 13, No. 8, Apr. 9, 2018, pp. 1257-1267, XP036559991, ISSN: 1861-6410, DOI: 10.1007/S11548-018-1732-8 [retrieved on Apr. 9, 2018].
Uneri, et al: "3D-2D image registration in virtual long-film imaging: application to spinal deformity correction", Progress in Biomedical Optics and Imaging, SPIE—International Society for Optical Engineering, Bellingham, WA, US, vol. 10951, Mar. 8, 2019, pp. 109511H-109511H, XP060121373, ISSN: 1605-7422, DOI: 10.1117/12.2513679, ISBN: 978-1-5106-0027-0.
International Search Report and Written Opinion dated Sep. 7, 2020 in corresponding/related International Application No. PCT/US2020/026124.
International Preliminary Report on Patentability dated Oct. 15, 2020 in corresponding/related International Application No. PCT/US2019/026014.
Japan Notice of Rejection corresponding to Japan Patent Application No. 2020-553543, Dispatch Date: Jan. 20, 2023.
Stayman J. W. et al., Model-based tomographic reconstruction of objects containing known components, Oct. 2010, IEEE Trans Medical Imaging, vol. 31, No. 10, pp. 1837-1848.
Xu S. et al., Polyenergetic known-component CT reconstruction with unknown with material compositions and unknown x-ray spectra, Mar. 28, 2017, Physics in Medicine & Biology, vol. 62, pp. 3352-3374.
Uenari A. et al., Known-component 3D-2D registration for quality assurance of spine surgery pedicel screw placement, Oct. 21, 2015, Physics in Medicine & Biology, vol. 60, No. 20, pp. 8007-8024.
Ruth Veikko et al., Metal Artifact Reduction in X-ray Computed Tomography Using Computer-Aided Design Data of Implant as Prior Information, Jun. 2017, Investigative Radiology, vol. 52, No. 6, pp. 349-359.

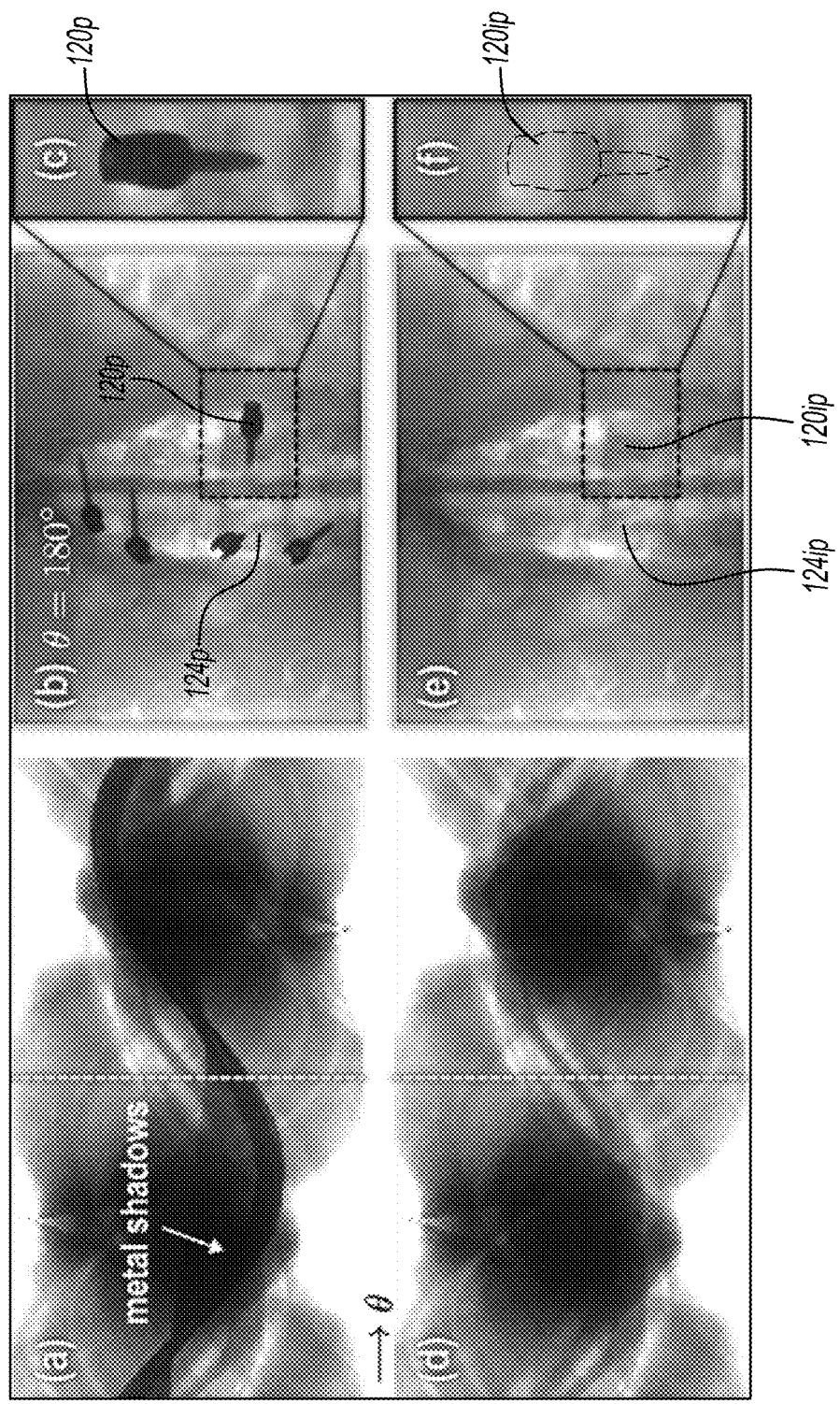
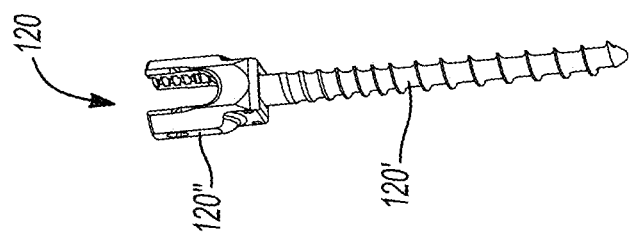
Fig-5

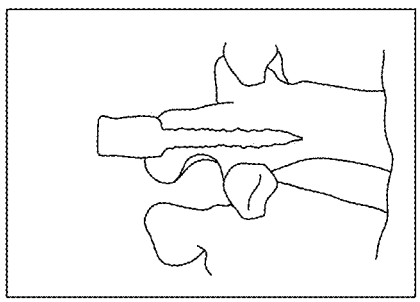
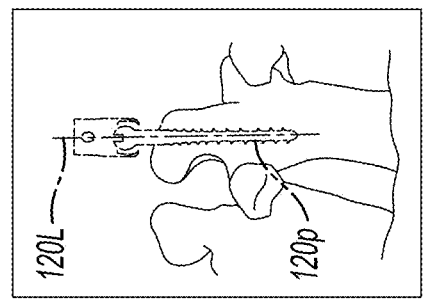
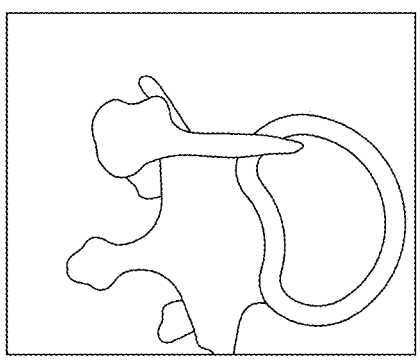
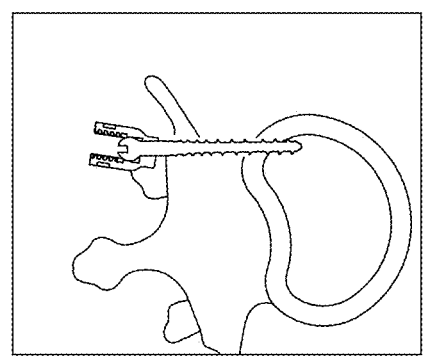
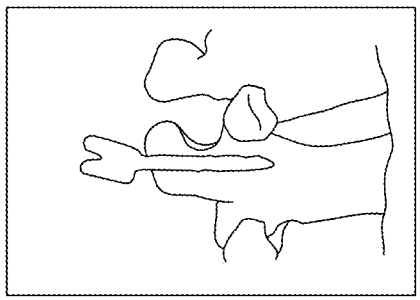
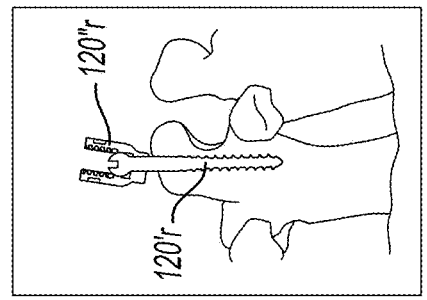
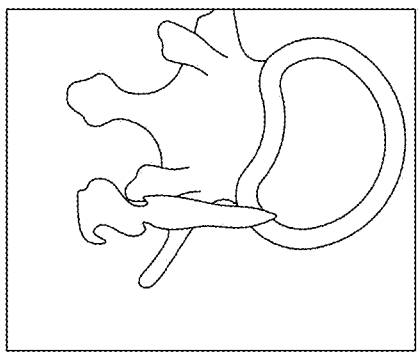
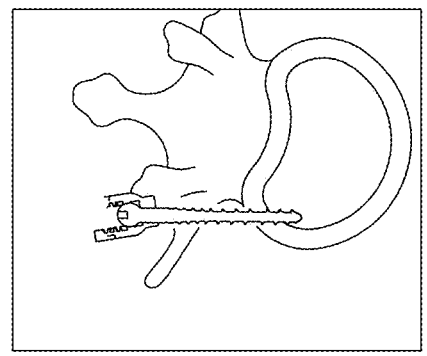
Fig-6

SYSTEM AND METHOD FOR ARTIFACT REDUCTION IN AN IMAGE

CROSS-REFERENCE TO RELATED APPLICATIONS

This application is a continuation of U.S. patent application Ser. No. 16/375,292, filed on Apr. 4, 2019, which claims the benefit of U.S. Provisional Application No. 62/654,038, filed on Apr. 6, 2018. The entire disclosure of the above applications are incorporated herein by reference.

GOVERNMENT LICENSE RIGHTS

This invention was made with government support under R01-EB-017226 awarded by National Institutes of Health. The government has certain rights in the invention.

FIELD

The subject disclosure relates to displaying an image, and particularly to correction or reduction of artifacts or distortion.

BACKGROUND

This section provides background information related to the present disclosure which is not necessarily prior art.

When acquiring image data or images of a selected object, such as a human patient, various artifacts or distortions may occur. For example, when acquiring X-ray based images of a subject, certain materials may interfere with X-rays in a manner disproportionate or different than other materials, such as tissue of a subject. For example, metal or polymer objects may attenuate and/or scatter X-rays in a manner different from the surrounding tissue of the subject. These effects of the non-tissue material may cause distortion or artifacts in the images generated with the acquired image data. The distortions may be amplified or easily viewed after a reconstruction, such as a three-dimensional reconstruction, based upon the two-dimensional projections of the subject. Correction of the distortions, therefore, may be selected in an attempt to generate images for viewing that are minimally distorted or without distortion.

SUMMARY

This section provides a general summary of the disclosure, and is not a comprehensive disclosure of its full scope or all of its features.

A subject may be imaged with a selected imaging system. In various embodiments, an X-ray imaging system may be used to acquire image data of the subject. The X-ray image data may be acquired according to various techniques, such as with an X-ray system that creates or acquires one or more two-dimensional projections. The two-dimensional projections may be used to generate a three-dimensional reconstruction. Accordingly, one or more two-dimensional projections may be acquired, such as in a sequence, to generate the three-dimensional reconstruction.

In acquiring the image data of the subject, the X-rays are attenuated by the material through which the X-rays pass from an X-ray source to a detector. The X-rays emitted from a source may be in a spectrum around an average or within a selected boundary. Accordingly, an X-ray source emitting X-rays at a selected energy, such as 120 kilo-electronvolts (keV), may actually be X-rays that are emitted at a range or in a spectrum around this amount. Accordingly, the attenuation may be different for each of the particular X-ray energies.

Further, similar materials may attenuate X-rays in a similar manner, such as soft tissue or hard tissue of a subject. Various non-tissue materials, such as metal objects (e.g. implants, instruments, etc.) may attenuate X-rays in a substantially different manner. For example, non-tissue materials may attenuate and/or reflect or scatter X-rays away from the item in the field of view (FOV) of the X-ray source or detector. It is understood that non-tissue materials may include items or materials other than metal, such a polymers, composite materials, or the like.

An image, such as a 2D projection, may include a plurality of effects (e.g. distortions) due to various non-tissue items within the FOV. The distortion may generate artifacts that are accumulated or magnified when generating a reconstruction based on a plurality of projections. Accordingly, removal of the distortions and the projections and inclusion of known effects of the selected components or items in the field of view may be inpainted to the rejections which are then used for the reconstruction. A reconstruction may include information based upon the facts of known components within an X-ray system to reduce or eliminate distortion and artifacts and a reconstruction.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5 is an illustration of a projection without and with inpainting; and

FIG. 6 is an illustration of a reconstruction without and with inpainting.

Corresponding reference numerals indicate corresponding parts throughout the several views of the drawings.

DETAILED DESCRIPTION

Example embodiments will now be described more fully with reference to the accompanying drawings.

Figure 1:
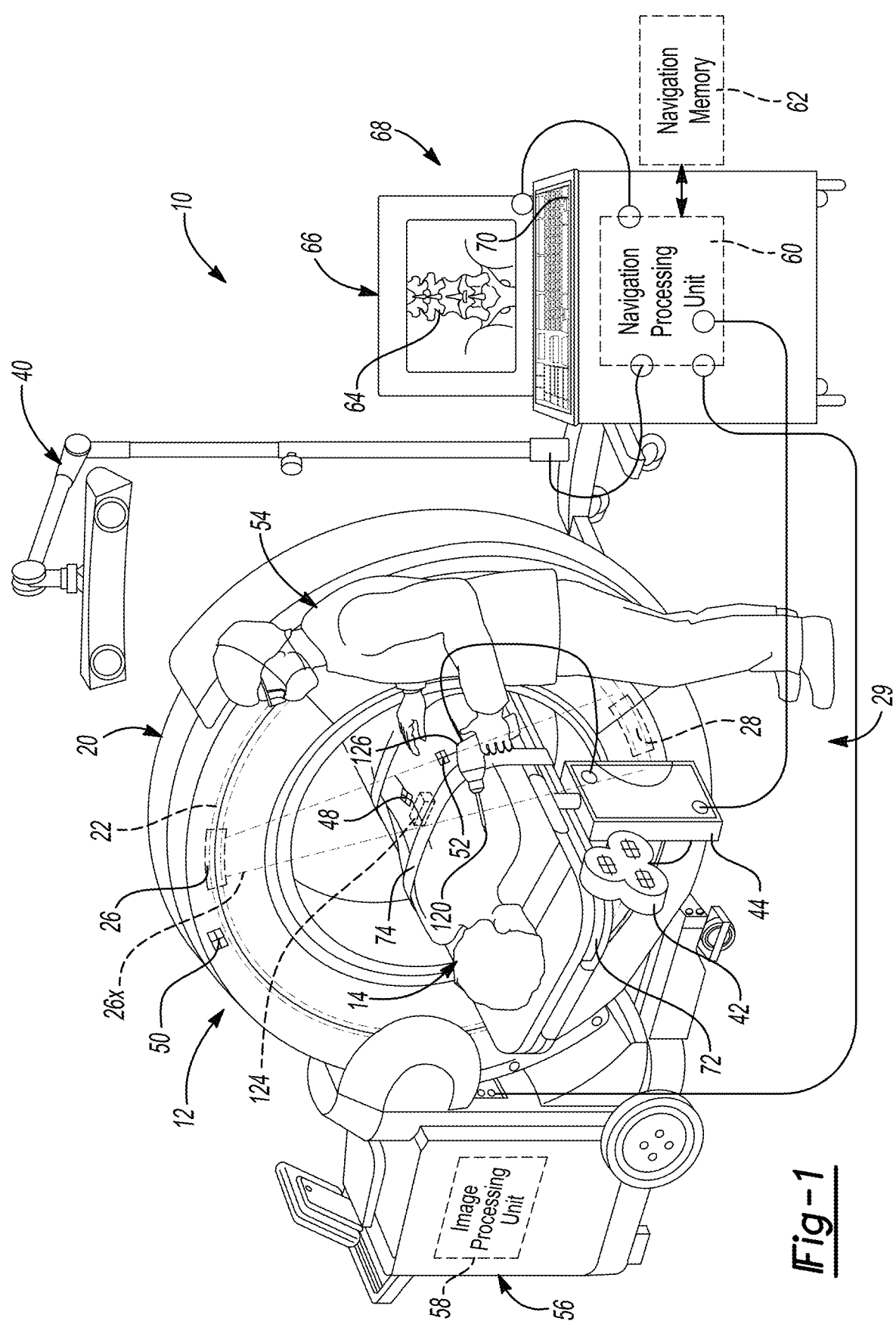
FIG. 1 is an environmental view of an operating theatre including an optional imaging system and a navigation system.
Figure 2:
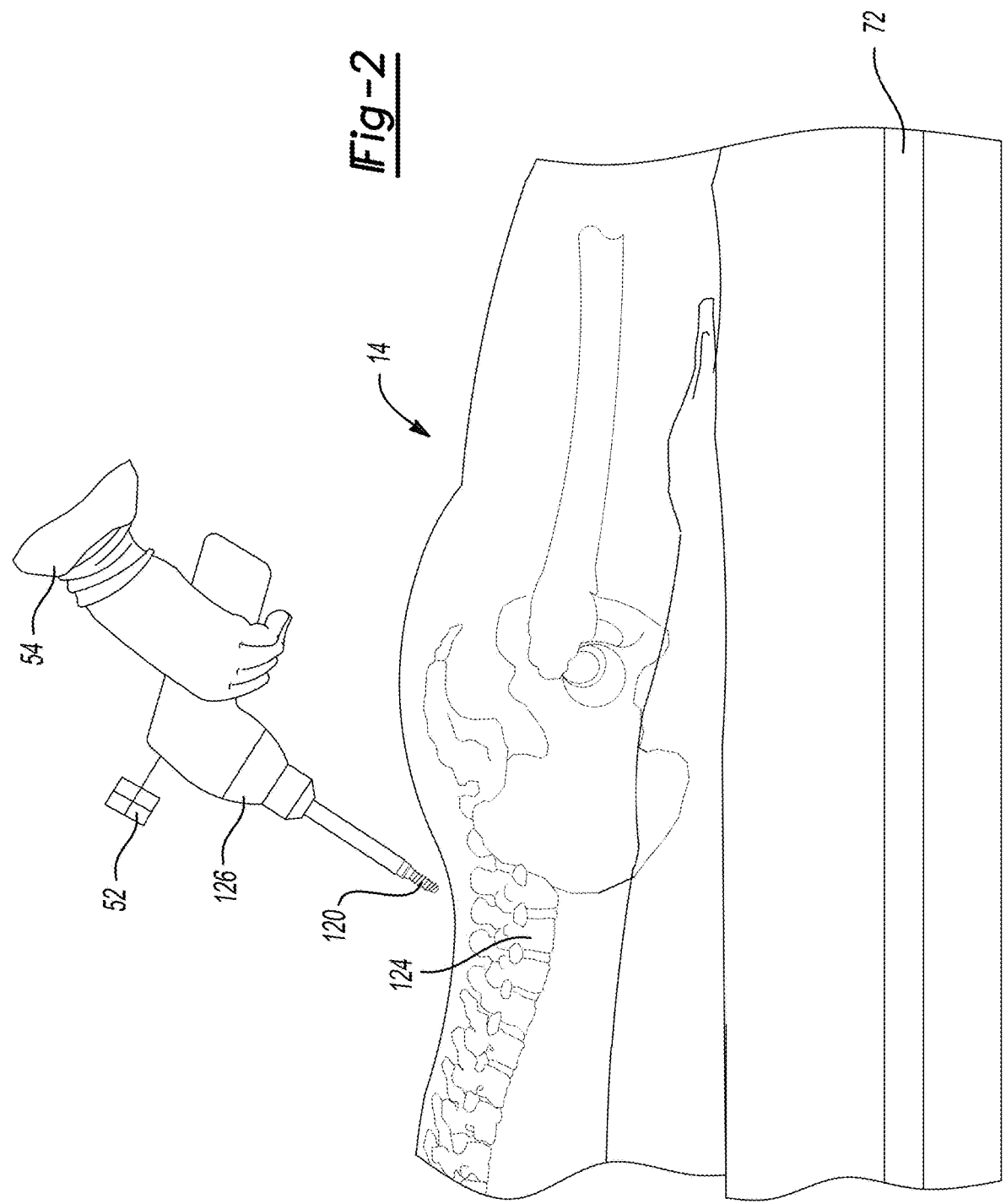
FIG. 2 is a schematic illustration of an instrument for inserting an implant into a patient.

With reference to FIG. 1 and FIG. 2, a diagram illustrating a procedure area is shown. The procedure area may include a surgical suite. Placed for use in the surgical suite may be a navigation system 10 that can be used for various procedures. The navigation system 10 can be used to track the location of an item, such as an implant or an instrument (as discussed herein), relative to a subject, such as a patient 14. It should further be noted that the navigation system 10 may be used to navigate any type of instrument, implant, or delivery system, including: guide wires, arthroscopic systems, orthopedic implants, spinal implants, deep brain stimulation (DBS) leads, cardiac pacing leads, ablation instruments, etc. Moreover, the instruments may be used to navigate or map any region of the body. The navigation system 10 and the various tracked items may be used in any appropriate procedure, such as one that is generally minimally invasive or an open procedure.

The procedure room may further include an imaging system 12. The imaging system 12 may, in various embodiments, interface with the navigation system 10. The imaging system 12 may be used to acquire preoperative, intraoperative, post-operative, or real-time image data of the patient 14. In various embodiments, the imaging system 12 may be used to acquire images at a selected time for confirmation and/or determining progress of a selected portion of a procedure. It will be understood by one skilled in the art, any appropriate subject can be imaged and any appropriate procedure may be performed relative to the subject. The subject 14 may be a human patient and the procedure may be a surgical procedure, such as an implantation of a device (e.g. a screw, lead, etc.).

Exemplarily illustrated in FIG. 1, the imaging system 12 comprises an O-arm® imaging device sold by Medtronic Navigation, Inc. having a place of business in Louisville, Colo., USA. The imaging device 12 may have a generally annular gantry housing 20 that encloses an image capturing portion 22. The image capturing portion 22 may include an x-ray source or emission portion 26 and an x-ray receiving or image receiving portion 28 (also referred to as a detector to detect the x-rays having past the subject 14) located generally or as practically possible 180 degrees from each other within the gantry housing 20. The x-ray emitting portion 26 may emit or generate a cone beam 26x of x-rays. The x-rays in the cone beam 26x will generally encompass a field-of-view, which may include at least a portion of the subject 14, such as a vertebra 124. The detector 28 may detect the x-rays that have passed through the subject 14. The x-rays may, however, be attenuated and/or scattered due to the subject or items in the cone beam 26x. Further, the detector may detect and/or generate two-dimensional (2D) image data or projections.

In various embodiments, the x-ray source or emission portion 26 and the x-ray receiving or image receiving portion 28 may be mounted on a rotor (not illustrated) relative to a track (not illustrated) within the generally annular gantry housing 20. The image capturing portion 22 can be operable to rotate 360 degrees during image acquisition. The image capturing portion 22 may rotate around a central point or axis, allowing image data of the patient 14 to be acquired from multiple directions or in multiple planes. The imaging system 12 can include those disclosed in U.S. Pat. Nos. 7,188,998; 7,108,421; 7,106,825; 7,001,045; and 6,940,941; all of which are incorporated herein by reference. The imaging system 12, however, may also include or be replaced with other imaging systems including C-arm fluoroscopic imaging systems, computer tomography (CT) imaging systems, etc. which can also generate three-dimensional views of the patient 14.

The position of the image capturing portion 22 can be precisely known relative to any other portion of the imaging device 12. In addition, as discussed herein, the precise knowledge of the position of the image capturing portion 22 can be used in conjunction with a tracking system 29 to determine the position of the image capturing portion 22 and the image data relative to the subject, such as the patient 14, which is tracked. For example a patient tracking device 48 may be placed on the patient 14 to track the patient 14.

The tracking system 29 can include various portions that are associated or included with the navigation system 10. The tracking system 29 can also include a plurality of types of tracking systems including an optical tracking system that includes an optical localizer 40 and/or an electromagnetic (EM) tracking system that can include an EM localizer 42. The optical localizer 40 may "view" or optically track trackable portions (tracking devices) with cameras. The EM localizer 42 may generate a field and a trackable portion (e.g. EM tracking device) may sense the field to determine a location relative to another tracking device in the field. Various tracking devices, including those discussed further herein, can be tracked with the tracking system 29 and the information can be used by the navigation system 10 to allow for a display of a position of an item. Briefly, tracking devices, such as a patient tracking device 48, an imaging device tracking device 50, and an instrument tracking device 52, allow selected portions of an operating theater to be tracked relative to one another with the appropriate tracking system 29, including the optical localizer 40 and/or the EM localizer 42.

It will be understood that any of the tracking devices 48, 50, 52 can be optical or EM tracking devices, or both, depending upon the tracking localizer used to track the respective tracking devices. It will be further understood that any appropriate tracking system can be used with the navigation system 10. Alterative tracking systems can include radar tracking systems, acoustic tracking systems, ultrasound tracking systems, and the like.

An exemplarily EM tracking system can include the STEALTHSTATION® AXIEM™ Navigation System, sold by Medtronic Navigation, Inc. having a place of business in Louisville, Colo. Exemplary tracking systems are also disclosed in U.S. Pat. No. 8,644,907, issued Feb. 4, 23012, titled "Method And Apparatus For Surgical Navigation"; U.S. Pat. No. 7,751,865, titled "Method And Apparatus For Surgical Navigation", issued Jul. 6, 2010; U.S. Pat. No. 5,913,820, titled "Position Location System," issued Jun. 22, 1999 and U.S. Pat. No. 5,592,939, titled "Method and System for Navigating a Catheter Probe," issued Jan. 14, 1997, all incorporated by reference herein.

Further, for EM tracking systems it may be necessary to provide shielding or distortion compensation systems to shield or compensate for distortions in the EM field generated by the EM localizer 42. Exemplary shielding systems include those in U.S. Pat. No. 7,797,032, titled "Method and system for navigating a catheter probe in the presence of field-influencing objects", issued on Sep. 14, 2010 and U.S. Pat. No. 6,747,539, titled "Patient-shielding and coil system", issued on Jun. 8, 2004, all of which are incorporated herein by reference. Distortion compensation systems can include those disclosed in U.S. Pat. No. 6,636,757, titled "Method and apparatus for electromagnetic navigation of a surgical probe near a metal object", issued on Oct. 21, 2003, all of which are incorporated herein by reference.

With an EM tracking system, the EM localizer 42 and the various tracking devices can communicate through an EM controller 44. The EM controller can include various amplifiers, filters, electrical isolation, and other systems. The EM controller 44 can also control the coils of the localizer 42 to either emit or receive an EM field for tracking. A wireless communications channel, however, such as that disclosed in U.S. Pat. No. 6,474,341, entitled "Surgical Communication Power System," issued Nov. 5, 2002, herein incorporated by reference, can be used as opposed to being coupled directly to the EM controller 44.

It will be understood that the tracking system may also be or include any appropriate tracking system, including a STEALTHSTATION® TREON®, and/or S7™ Navigation System having an optical localizer, similar to the optical localizer 40, sold by Medtronic Navigation, Inc. having a place of business in Louisville, Colo. Optical tracking systems may also include those discloses in U.S. Pat. No. 8,010,177, Aug. 30, 2011, Intraoperative Image Registration"; U.S. Pat. No. 6,235,038, issued on May 22, 2001, titled "System For Translation Of Electromagnetic And Optical Localization Systems", all incorporated herein by reference. Further alternative tracking systems are disclosed in U.S. Pat. No. 5,983,126, to Wittkampf et al. titled "Catheter Location System and Method," issued Nov. 9, 1999, which is hereby incorporated by reference. Other tracking systems include an acoustic, radiation, radar, etc. tracking or navigation systems.

The imaging system 12 can include a support housing or cart 56. The imaging system 12 can further include a separate image processing unit 58 that can be housed in the cart 56. The navigation system 10 can include the navigation processing unit 60 that can communicate or include a navigation memory 62. The navigation member 62 may include any appropriate non-transitory memory including a random access memory, magnetic media drive, etc. Further, the navigation memory 62 may be integrated with the navigation processing unit 60 or remote from the navigation processing unit 60. The navigation processing unit 60 can receive information, including image data, from the imaging system 12 and tracking information from the tracking systems 29, including the respective tracking devices 48-52 and the localizers 40-42. Image data can be displayed as an image 64 on a display device 66 of a workstation or other computer system 68.

The workstation 68 can include appropriate input devices, such as a keyboard 70. It will be understood that other appropriate input devices can be included, such as a mouse, a foot pedal or the like. Further, the various processing units, as discussed above, may be incorporated into the workstation or computer system 68. Thus, the various inputs may be used by the user 54 to include commands to the system. Further, the navigation member 62 or other appropriate and/or similar memory may be used to transfer or for recall of information, such as image data and/or instructions for execution by the selected processing units. The various processing units, computers, and/or workstations may include internal or local memory and processing units. The processing units may include central processing units that are general computers that execute instructions to perform tasks on a chip. The processing units may also be specific circuits, such as application specific integrated circuits (ASIC). Accordingly, the processing units may be devices that receive information and execute instructions that are stored or received based on the information. Further, the memories may include transient and non-transient memory systems, such as random-access memory, volatile or non-volatile memory, etc.

The image processing unit 58 may process image data from the imaging system 12 and may transmit the image data, before or after selected processing, to the navigation processing unit 60. It will be further understood, however, that the imaging system 12 need not perform any image processing and it can transmit the image data directly to the navigation processing unit 60. Accordingly, the navigation system 10 may include or operate with a single or multiple processing centers or units that can access single or multiple memory systems based upon system design. Moreover, the processed image data, as discussed herein, may be displayed on the display device 66 or any appropriate display device. Thus, the displayed images need not be displayed with a navigation system 10.

The patient 14 can be fixed onto a support 72, such as an operating table, but is not required to be fixed to the table 72. The table 72 can include a plurality of straps 74. The straps 74 can be secured around the patient 14 to fix the patient 14 relative to the table 72. Various apparatuses may be used to position the patient 14 in a static position on the operating table 72. Examples of such patient positioning devices are set forth in commonly assigned U.S. patent application Ser. No. 10/405,068, published as U.S. Pat. App. Pub. No. 2004/0199072, entitled "An Integrated Electromagnetic Navigation And Patient Positioning Device", filed Apr. 1, 2003, which is hereby incorporated by reference. Other known apparatuses may include a Mayfield® clamp.

Also, the position (including three-dimensional location and orientation) of the patient 14 relative to the imaging system 12 can be determined by the navigation system 10 with the patient tracking device 48 and the imaging system tracking device 50. As discussed herein, the position (including three-dimensional location and orientation) relative to the patient 14 may be determined, at least in part, with images acquired of the patient 14. Accordingly, the position (including three-dimensional location and orientation) of the patient 14 relative to the imaging system 12 can be determined. The imaging system 12, such as the O-arm® can know its position and be repositioned to the same position within about 10 microns. This allows for a substantially precise placement of the imaging system 12 and precise determination of the position of the imaging device 12. Precise positioning of the imaging portion 22 is further described in U.S. Pat. Nos. 7,188,998; 7,108,421; 7,106,825; 7,001,045; and 6,940,941; all of which are incorporated herein by reference. Generally, it may be selected to determine the position of the image data relative to the patient 14. For example, the position, including the orientation relative to the patient, of the image data may be used to determine a location of a portion of the patient 14.

Subject or patient space and image space can be registered by identifying matching points or fiducial points in the patient space and related or identical points in the image space. The imaging device 12, such as the O-arm® imaging device sold by Medtronic Navigation, Inc., can be used to generate image data at a precise and known position. This can allow image data that is automatically or "inherently registered" to the patient 14 upon acquisition of the image data. Essentially, the position of the patient 14 is known precisely relative to the imaging system 12 due to the accurate positioning of the imaging system 12 relative to the patient 14. This allows points in the image data to be known relative to points of the patient 14 because of the known precise location of the imaging system 12.

Alternatively, manual or automatic registration can occur by matching fiducial points in image data with fiducial points on the patient 14. Registration of image space to patient space allows for the generation of a translation map between the patient space and the image space. According to various embodiments, registration can occur by determining points that are substantially identical in the image space and the patient space. The identical points can include anatomical fiducial points or implanted fiducial points. Exemplary registration techniques are disclosed in U.S. Pat. No. 9,737,235, issued Aug. 22, 2017, incorporated herein by reference.

In various embodiments, the navigation system 10 may be used to assist in performing a procedure. It is understood, however, that the navigation system 10 is not required. In various embodiments, a procedure may proceed without the navigation system. The procedure, however, may also use, alone or in combination with the navigation system 10, the imaging system 12, can be used to perform selected procedures. Selected procedures can use the image data generated or acquired with the imaging system 12. Further, the imaging system 12 can be used to acquire image data at different times relative to, such as during, the procedure. As discussed herein, image data can be acquired of the patient 14 subsequent to a selected portion of a procedure for various purposes, including confirmation of the portion of the procedure.

With continuing reference to FIG. 1, the imaging system 12 can acquire image data, such as projections of the subject 14. The projections may include 2D projections that are able to be displayed as 2D images. The imaging system 12 may also be used to generate or reconstruct three dimensional (3D) images of the patient 14. The patient 14 can be placed relative to the imaging system 12 to allow the imaging system 12 to obtain image data of the patient 14. To generate 3D image data, the image data can be acquired from a plurality of views or positions relative to the patient 14. The positions may be positions around the patient 14, such as separated by angles by movement of the detector 28 relative to the subject 14. Each position may be defined or referred to as an angle or theta (θ) position relative to the patient 14. The 3D image or image data of the patient 14 can be used alone or with other information to assist in performing a procedure on the patient 14 or an appropriate subject. It will be understood, however, that any appropriate imaging system can be used, including magnetic resonance imaging, computed tomography, fluoroscopy, etc. to acquire image data (including 3D image data) of the patient 14.

As discussed above, the imaging system 12 may include any appropriate imaging system, such as the O-arm® Imaging System sold by Medtronic Navigation, Inc. The O-arm® Imaging System can acquire images of the subject 14 by acquiring image data of the subject 14 that may include two-dimensional projections. The projections are acquired by emitting X-rays from the source 26 and detected at the detector 28. The projections may be displayed as two-dimensional images on the display device 66 and/or may be reconstructed into a three-dimensional image, such as the image 64, for display on the display device 66. The image, for example the reconstructed image 64, may include artifacts or distortion if various items are positioned within the field of view of the imaging system, such as within the cone of X-rays 26x emitted from the X-ray source 26 and detected at the detector 28. This distortion refers not only to the spatial distortion in the reconstructed image, but also includes distortion of the signal recorded by the detector—e.g., polyenergetic effects (beam hardening) associated with energy-dependent detector response, and "zero" data or electronic noise contribution (photon starvation effects). Distortions may be generated when various non-tissue elements or materials, such as a pedicle screw 120 that may be driven or moved with an instrument, such as a surgical motor 126, are within the X-ray cone 26x when the subject 14 imaged. For example, according to various embodiments, the pedicle screw 120 may be implanted into a vertebra 124 in the patient 14. It is understood that discussion herein to a single or plural vertebrae is merely exemplary and generally a procedure maybe performed on any selected number of appropriate vertebrae. The pedicle screw 120 may be positioned in the vertebra 124 during a surgical procedure, as is generally understood in the art. The imaging system 12 may then be used to acquire images after placing the pedicle screw 120 in the subject 14, but prior to completing a procedure, such as placing a connection rod, or other selected portion of a procedure. Imaging the subject 14 while the pedicle screw 120 is in place, distortion may occur in the image projection that causes further distortion and/or artifacts in the image reconstruction 64 for display on the display device 66. According to various embodiments, therefore, a process may be performed, such as by instructions executed by the navigation processing unit 60 and/or the imaging processing unit 58 or other appropriate processor, to assist in removing the artifacts and/or accounting for the artifacts for displaying a non-distorted image.

The process of removing or accounting for the distortion in the images may be initiated by accounting for or determining artifacts or distortion in a projection due to a selected item, such as an object including an implant or instrument. The selected item may then be replaced in projections prior to a reconstruction, where the replacement can be performed according to a variety of inpainting methods. The process may be developed into an algorithm and instructions based thereon that are stored in a memory, such as the navigation memory 62 or other appropriate memory, and executed by one or more processors or processing units, including those discussed above. A reconstruction with the correction or artifact reduction may then be displayed on the display device 66 as the image 64.

Figure 3:
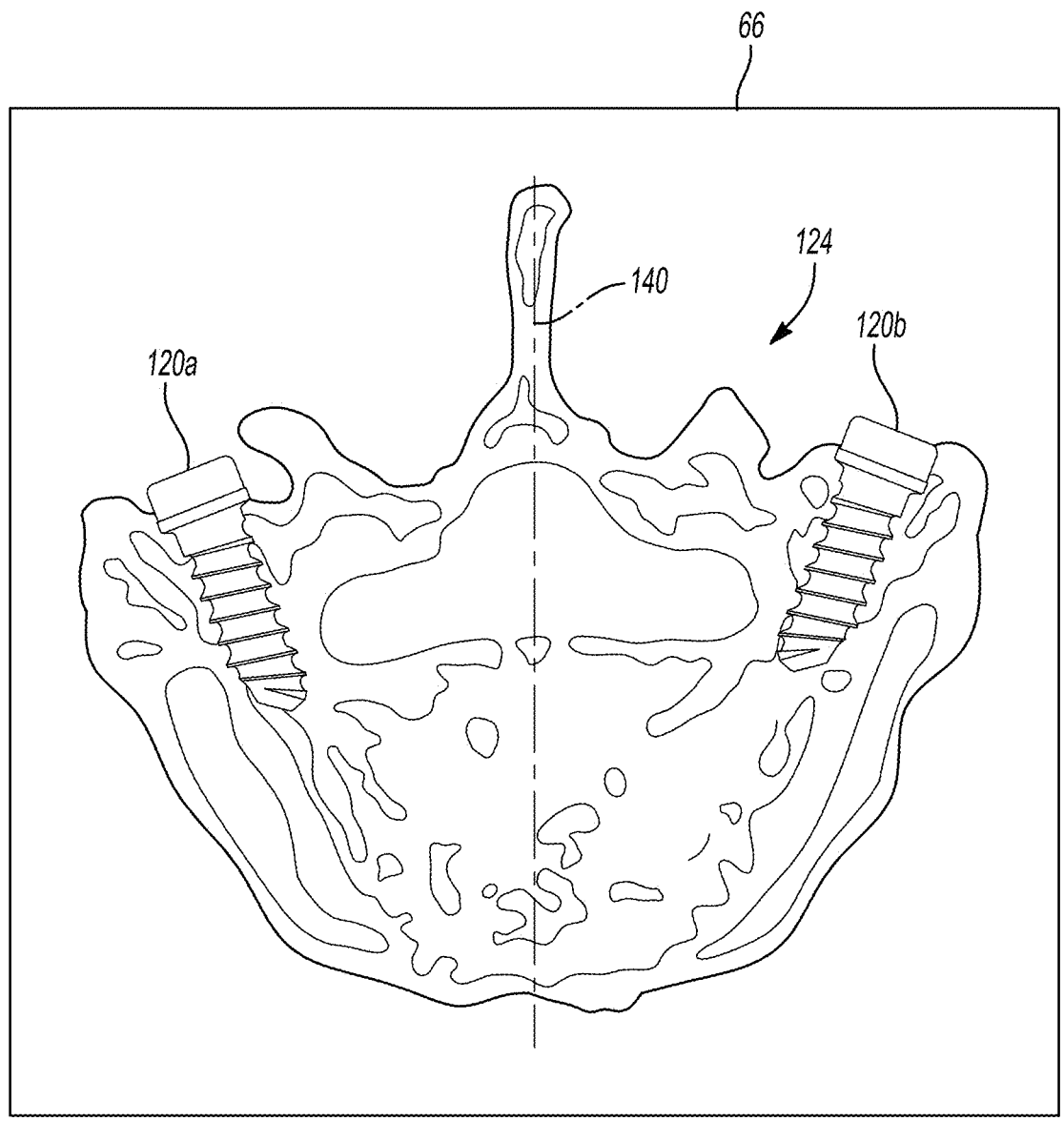
FIG. 3 is a schematic illustration of an implant in a subject.

As discussed above, images may be generated and viewed on the display device 66. The acquired images are acquired with the imaging system 12, which may include the O-arm® Imaging System, at a selected time. For example, the images may be acquired during a selected procedure, such as an operative procedure on the subject 14. In various embodiments, the operative procedure may include positioning an implant into the patient 14. The implant may include the pedicle screw 120, or more than one pedicle screw 120, positioned in one or more vertebrae 124. As illustrated, exemplary, in FIG. 3, first and second pedicle screws 120a and 120b are schematically illustrated positioned in the vertebra 124 relative to a midline 140. The midline 140 may be displayed on the display device 66 relative to an image, such as the image 64, or may be exemplary of a midline extending from a posterior to an anterior portion of the patient 14. After positioning the pedicle screw 120 in the patient 14, such as in the vertebra 124, the imaging system 12 may be used to acquire image data of the patient 14, including the vertebra 124 having the pedicle screws 120a and 120b positioned therein. As illustrated in FIG. 3, the pedicle screw 120 may be positioned in the vertebra 124 in any appropriate manner, such as with the drill motor or tool 126 by the user 54.

Acquiring image data of the subject 14 after positioning the pedicle screw 120 in the patient may be performed for any appropriate purpose, such as confirmation of positioning the pedicle screw 120 in a selected or predetermined position. During image data acquisition, particularly after the pedicle screws 120a, 120b are placed, distortion or artifacts in the image 64 may hinder or slow confirmation of the correct or accurate position of the pedicle screw 120 in the vertebrae 124. Accordingly, as discussed further herein, a selected process may be used to reduce and/or correct for distortion or errors in the acquired image data before or prior to generating the image 64, which may include a reconstruction such as a three-dimensional reconstruction, based upon one or more projections acquired of the subject 14 with the imaging system 12.

Figure 4:
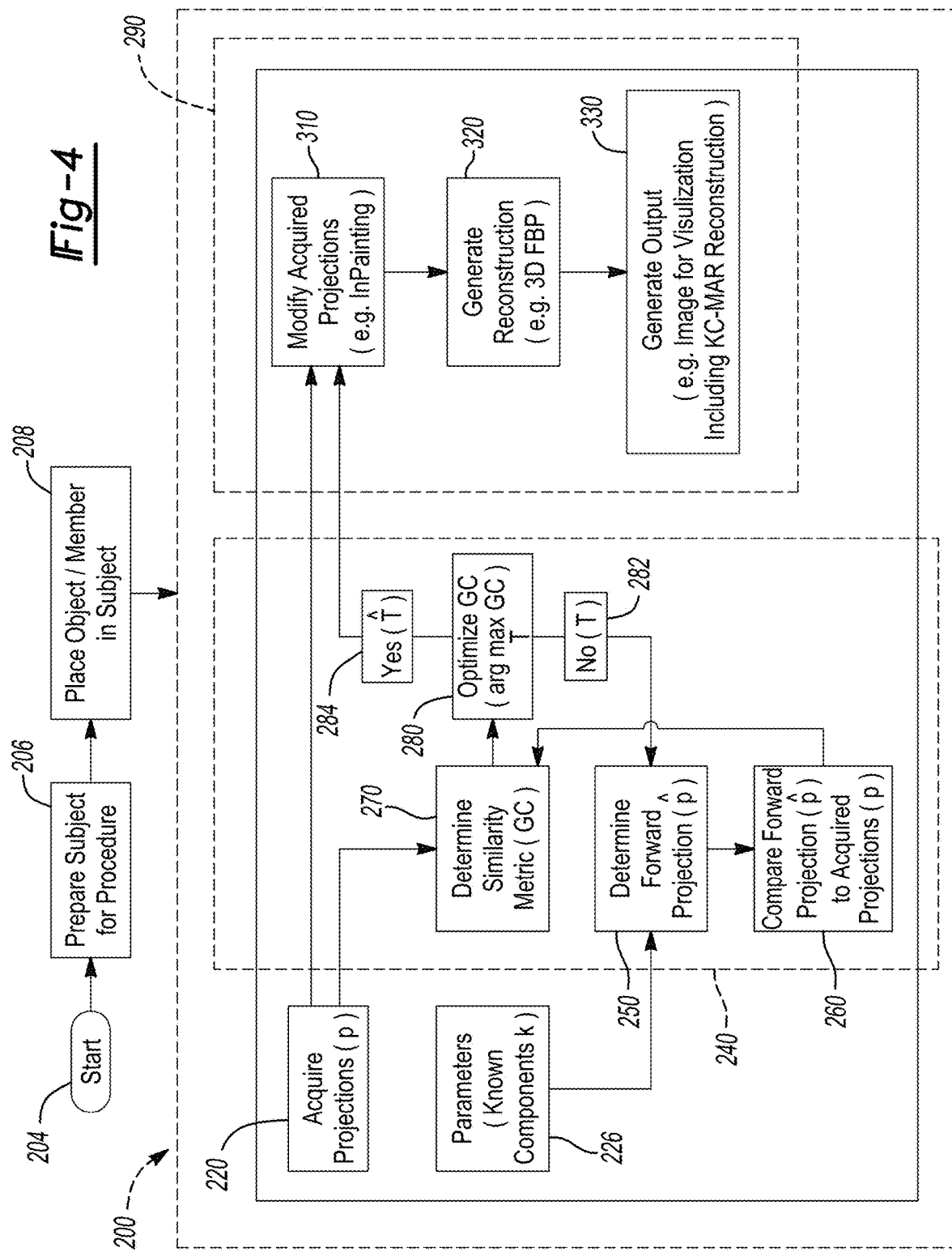
FIG. 4 is a flowchart of a process for reducing artifacts or distortion in an image.

Turning reference to FIG. 4, a process or flowchart 200 illustrates an efficient process for removing or accounting for artifacts in projections and later reconstructions, such as the image 64, of the subject 14 for viewing by the user 54. The process 200 allows for an efficient, including lower computational time and/or necessary resources, to generate the image 64 for viewing by the user 54 without artifacts and/or showing a clear or high contrast edge of a selected item. In various embodiments, the selected item may include the pedicle screw 120 positioned in the vertebra 124. In various embodiments, computational time may be lowered to less than about three minutes, including less than about two minutes for generating a reconstruction with inpainted objects, as discussed herein, with the process 200. The removal of the artifacts may allow for a more precise and clear image and/or distinction between the selected item, such as the pedicle screw 120 and in surrounding areas, such as the vertebra 124. It will be understood that the positioning of the pedicle screw 120 in the vertebrae 124 is exemplary and contrast and/or distortions may occur between any differing materials. Accordingly, discussion of the pedicle screw 120 relative to the vertebrae 124, herein, is exemplary unless specifically identified otherwise.

Also, it is understood that the pedicle screw 120 may be formed of one or more selected material (e.g. metal or metal alloy) that affects X-rays when generating X-ray image data in a manner to cause distortion or artifacts relative to the X-rays that generate the image data of the vertebrae 124. Therefore the process 200 may be used to remove or account for the artifacts in the image data when generating the image 64 for display with the display device 66. It is further understood that the pedicle screw 120, or other selected item, may be formed of or include a plurality of materials.

With continued reference to FIG. 4 the process 200 is understood to be an image analysis and/or reconstruction process 200 that may be performed alone and/or in part of a selected procedure, such as a surgical procedure including positioning the pedicle screw 120 in the vertebrae 124. The process 200, therefore, may also be an algorithm, or include algorithmic portions, that may be executed by a selected processor or processor system, such as the imaging processing unit 58 discussed above. It is understood, however, that any appropriate processing system may be used to execute the process 200 to generate an image for display on the display device 66.

The process 200 may be incorporated into other procedures, such as a surgical procedure including placing a selected item, such as the pedicle screw 120. The selected procedures, therefore, may include starting a procedure in block 204 and then preparing a subject for procedure in block 206. Preparing the subject for procedure in block 126 may include predetermining or selecting a location for the pedicle screw 120, or other appropriate implant, within the subject 14. Such preplanning or predetermination may include acquiring preoperative image data of the subject 14 and planning a position for the pedicle screw 120 in the vertebra 124. Further, preparing the subject may include moving the subject 14 into the operating theatre on the support 72, forming an incision of the subject 14, positioning instruments relative to the subject 14, or other appropriate procedure steps.

After preparing a subject for a procedure in block 206, placing a selected item in the subject in block 208 may be performed. As discussed above, exemplary embodiments may include positioning the pedicle screw 120 in the vertebra 124, as illustrated in FIG. 2. The pedicle screw 120 may be any appropriate pedicle screw such as a CD Horizon® Solara® or Legacy® spinal or pedicle screws, sold by Medtronic, Inc. having a place of business in Minnesota, USA.

With additional reference to FIG. 5, the pedicle screw 120 may include selected portions, such as a first shank portion 120' that is positioned within the vertebrae and/or a second portion 120", such as a head or gimbal head portion that is movable relative to the shank. It is understood, however, that the pedicle screw 120 may be any appropriate type of pedicle screw positioned in the patient. It is further understood that the selected item positioned in block 208 need not be a pedicle screw, but may be any appropriate type of item positioned relative to the subject 14, or any other appropriate portion. Generally the selected item, such as the pedicle screw 120, is formed of a different material (e.g. metal) than the portion in which it is placed, such as the vertebrae 124 (e.g. bone tissue).

After positioning the selected item in block 208, the process 200 may be used to assist in generating a selected or appropriate reconstruction for viewing by the user 54. The process 200 may include or start with the acquisition of projections including the selected items in block 220. The acquisition of projections in block 220 may include the acquisition of two-dimensional projections of the subject 14. The acquisition may be a real time image data acquisition, recalling of image data, or a combination of both. With continuing reference to FIG. 5, projections that are acquired may include those shown in parts (a), (b), and (c). The projections may include the vertebra 124 and the pedicle screw 120.

As illustrated in FIG. 5, the pedicle screw 120 is schematically or exemplary illustrated. The pedicle screw 120 may include various features such as the shank 120' the head 120" and other portions. The shank 120' may include a thread or other feature to allow for purchase or connection with the vertebra 124. The head 120" may include additional features, such as a U-shape and be moveable relative to the shank 120'. The head 120" may then be fixed to the shank 120' in a selected manner, such as with a set screw or a nut. It is understood that the shank 120' and the head 120" may be formed of the same material or a different material, such as two different metal alloys or one metal and one polymer.

Nevertheless, the pedicle screw 120 may be positioned in the vertebra 124 and images may be acquired of the vertebrae 124 and the screw 120 positioned therein. For example, as illustrated in FIG. 5, part (b) one or more of the pedicle screws 120 may be positioned may be positioned in the patient, such as the vertebra 124. As illustrated in FIG. 5 the image of the vertebra $124p$ is shown and the image of the pedicle screw $120p$ is shown. The projection may include a two-dimensional projection generated with the imaging system 12 in the field of view. It is understood, however, a plurality of projections, for example including about 360 projections, may be generated of the subject 14 in the field of view including the vertebrae 124 and the pedicle screw 120. Any appropriate selected number of projections, however, may be acquired and included in the process 200. For example, the projection in (b) is denoted as theta ($\theta$)=180 degrees (°), and, therefore, may be a projection acquired at 180° from an origin or start point.

As discussed further herein, the projections, as illustrated in FIG. 5, may include a plurality of projections that are acquired in any appropriate manner. For example, as discussed above, the process 200 may be executed with the image processing unit 58. Accordingly, the imaging system 12 may generate or collect the image data including the projections and they may be immediately processed with the imaging processing unit 58. Alternatively thereto, or in addition thereto, the image data may be acquired with the imaging system 12 and then may be forwarded or transferred to selected processing units or processors. For example, the image data may be transferred with a coupling, such as a wired or wireless protocol, saved to a selected memory medium (e.g. CD-ROM, volatile or nonvolatile memory, etc.). Accordingly, it is understood by one skilled in the art, that the acquiring projections in block 220 may include operating the imaging system 12 to acquire image data, receiving image data from a selected memory, or transferring the image data from a selected memory or source to a sourcing unit.

Regardless of the particular method of acquiring the projections in block 220 that may be further processed, as discussed herein. Each of the projections from block 220 may be distorted, in the sense that the signal levels recorded by the detector 28 are inaccurate. The distortion leads to artifacts in the 3D images reconstructed from those projections, such as streaking or shadows, due to the material of the pedicle screw 120 in the field of view, including the cone 26x of X-rays. In FIG. 5 the part (c) illustrates a close up or detail view of an area of interest (AOI) or field of interest.

The acquisition of the projections in block 220 may include a first input for the process 200. Additional inputs may include known component parameters or known components (KC) in block 226. The known component parameters may be predetermined parameters of the selected item, such as the pedicle screw 120. In various embodiments, for example, the KC may include the pedicle screw 120 having the shank 120' and the head 120". The known component parameters may further include the type of material of the selected portions of the pedicle screw 120, such as the shank 120' formed of a stainless steel alloy and the head 120" being formed of the same stainless steel alloy. It is understood, however, that the pedicle screw, such as the shank 120', may be formed of other materials such as titanium or titanium alloys, polymers, or the like. Nevertheless, the known parameters in block 226 may include the specifics of the selected item, such as the pedicle screw 120.

The known parameters in block 226 may also include selected dimensions such as length, width, height, and the like. The known parameters in block 226 may further include the number of components or portions of the pedicle screw 120 and the relative geometry of the various components or portions of the pedicle screw. For example, the known parameters in block 226 may include a fixed geometry of the pedicle screw 120 and/or various possible geometries of the pedicle screw 120. As illustrated in FIG. 5, the pedicle screw 120 includes the shank 120' and the head 120" movable relative to one another. Accordingly, the known parameters in block 226 may include a range of motion and/or degree of freedom of motion (e.g. possible geometries) of the shank 120' relative to the head 120".

The known parameters in block 226 may further include known interactions of X-rays relative to the selected item, including the pedicle screw 120. The known parameters in block 226 may include the known interactions of X-rays with the stainless steel forming the shank 120' and the stainless steel forming the head 120". The known parameters in block 226 may further include interactions of X-rays with titanium or titanium alloys, polymers, or other materials that may form the pedicle screw 120. The known interactions of the KC may include the amount of attenuation, the amount of scattering, the amount of absorption, or other selected parameters of X-rays relative to materials of the pedicle screw 120. The known component parameters may be determined via testing prior to the process 200 and saved for further access. Further, the KC may relate to a specific item, such as the pedicle screw 120, that is input or used to select a specific, including singular, KC in block 226.

The known component parameters, also referred to as parameters of the component or object (e.g. the pedicle screw 120), may be defined in various manners, such as those discussed above, including exact values and/or defined or determined during a selected process. Exact values or parameters may be based upon specifications of the object (e.g. predetermined and/or known technical specifications of the object). The specifications of the object may include the features, such as those identified above, including a length, diameter, interaction with a polyenergetic x-ray beam, or other features. These values may be exact or nearly exact, such as knowing the exact width or range length, diameter, or the like, such as within selected tolerances. In various embodiments, however, the parameters may also be determined or defined during a selected process. As discussed herein, the object may be determined or registered in the projections based upon a selected process, as discussed further herein. During the registration process the object may be parametrically defined and/or determined in the acquired projections. By defining the parameters during a registration process, a determination may be made during the selected procedure of the parameters including a length, diameter, or the like. These may be based upon analysis of the image or require projections based upon selected known or assumed interactions with an x-ray beam, or other features. Accordingly, the parameters may be predetermined, as discussed above and noted herein, and/or determined during a registration process by analyzing the image data acquired in the projections.

In various embodiments, therefore, the known component parameters in block 226 may be representations, such as a lookup table, of the selected item including the pedicle screw 120. Further, the known parameters in block 226 may include selected specific models, such as a computer aided design (CAD) model of the pedicle screw 120 including known materials thereof and known interactions of X-rays relative thereto. In various embodiments, the pedicle screw 120 is the CD Horizon® Solara® implantable pedicle screw and the known component parameters in block 226 may include a CAD model of the specific pedicle screw (including a specific model number and/or geometry and dimensions thereof) or a deformable spline model (such as a spline model of a cylindrical wire, needle, or rod) along with known materials, known interaction of materials, and the like. The known parameters in block 226 may then be accessed, such as recalled with the processing unit 58, for further portions of the process 200.

With continued reference to FIG. 4, once the projections are acquired in block 220 and the known parameters are acquired or accessed in block 226, a registration, also referred to as a known component (KC) registration may occur in a sub-block or sub-process 240. The KC registration in block 240 may include various steps or processes including a forward projection in block 250. The forward projection in block 250, as discussed further herein, may then be compared to the projections in block 260. Based upon the comparison in block 260 a similarity metric (GC) may be determined in block 270. The comparison in block 260, yielding the similarity metric in block 270, may then be optimized in block 280. In particular, the optimizer block 280 may generate a transformation that is again applied to a forward projection in block 250 to determine a similarity metric in block 270 based upon a comparison in block 260.

Accordingly, the KC registration in block 240 is an iterative process until the optimizer in block 280 determines an optimized transformation.

An optimized transformation may be a convergence where the differences between the forward projection in block 250 and the projections in block 260 are substantially small or have a selected similarity metric in block 270. At the selected transformation of similarity metric, the transformation is determined to have converged or been optimized as an optimized transform ($\hat{T}$) and may be used for a reconstruction process 290. The reconstruction process 290 is understood to be a sub-process of the artifact or noise reduction process 200. The reconstruction process 290 will be discussed further herein and, briefly, generally combines the acquired projections from block 220 with the optimized or converged transform from block 280.

Returning to the KC registration process 240, the KC registration process 240 includes a registration of the known components from block 226 with a selected number of projections, including less than or all of the acquired projections from block 220, that may be used for a later reconstruction in the reconstruction sub-process 290. In particular, the KC registration attempts to determine the portion in the acquired projections from block 220 that match to the known component in block 226. For example, one or more pixels in one or more of the projections are generated by the selected item (e.g. pedicle screw 120) positioned within the subject in block 208 and therefore should match a forward projection of the known component from block 226. For example, as discussed above, the pedicle screw 120 may have precise parameters known that define the known component parameters in block 226. Accordingly, the known parameters may be input as represented by K. A digital radiograph reconstruction or digitally reconstructed radiograph (DRR) forms the forward projection in block 250 and may be defined by Equation 1 (Eq. 1):

$$\hat{p}(\kappa, T) = \int_{\vec{r}} \kappa(T) d\vec{r}^2 \quad \text{Eq. 1}$$

In Eq. 1, the forward projection $\hat{p}$ is a projection of the known component. In particular, Eq. 1 includes a DRR formed from the input known parameters κ from block 226, which may include a mesh model of the selected item that is a line integral along a ray $\vec{r}$ incident on the transformed KC κ. Accordingly, the forward projection $\hat{p}$ is a digitally reconstructed radiograph (also referred to as a mask herein) based upon the known component parameters κ from block 226 that may be compared to the acquired projection (also referred to herein as p). One or more selected transformation models (T) may be employed, such as a rigid homogeneous transform or a deformable b-spline function. Generally, only one transformation model may be selected in any specific application, but various appropriate models may be selected or the transformation (T). Furthermore, select parameters of κ may be included within the optimization process, for example to model the unknown diameter of a tool with a cylindrical profile.

The forward projection as defined in block 250 may be compared in block 260 to the acquired projections p from block 220. The comparison in block 260 may allow for the output of the similarity metric which, in various embodiments, is defined as a gradient correlation (GC). While GC, according to Equation 2 (Eq. 2), is an appropriate similarity metric, it is understood that other similarity metrics may also be used. Regarding GC, however, Eq. 2 includes:

$$GC(p, \hat{p}) = \frac{1}{2}\{NCC(\nabla_x p, \nabla_x \hat{p}) + NCC(\nabla_y p, \nabla_y \hat{p})\} \quad \text{Eq. 2}$$

and Equation 3 (Eq. 3):

$$NCC(a, b) = \frac{\Sigma_i (a_i - \bar{a})(b_i - \bar{b})}{\sqrt{\Sigma_i (a_i - \bar{a})^2} \sqrt{\Sigma_i (b_i - \bar{b})^2}} \quad \text{Eq. 3}$$

The GC generally looks for gradients (also referred to as high contrast regions or edges) between the forward projection $\hat{p}$ in block 250 and the acquired projections in block 220. According to Eq. 2 and Eq. 3, the GC is defined as a sum of normalized cross-correlation (NCC) of orthogonal image gradients. For example, the NCC defines the correlation of the normalized intensities of image gradients a and b for images p and p, respectively. Therefore, the GC, as illustrated in Eq. 2, is a sum of the gradients between the forward projection from block 250 and the acquired projections from block 220.

The optimizer in block 280 is then used to determine whether the converged transform $\hat{T}$ has been found or achieved. In particular, the convergence is defined by Equation 4 (Eq. 4):

$$\hat{T} = \underset{T}{\text{argmax}} \sum_\theta GC(p_\theta, \hat{p}_\theta(\kappa, T)) \quad \text{Eq. 4}$$

which may be iteratively solved between the forward projection in block 250 and the acquired projections from block 220. Eq. 4 is used to determine the greatest similarity between the forward projection in block 250 and the acquired projections in block 220. The iteration occurs by determining the GC in block 270 based upon the comparison in block 260 and then transforming the forward projection from the optimizer in block 280 to a different forward projection in block 250. Accordingly, the optimizer block may determine whether the similarly metric in block 270 is the same or has been optimized and/or within a selected threshold of change, for example when the mean change in T is smaller than about 0.01 millimeters (mm) to about 0.2 mm, including about 0.1 mm and about 0.01 degrees to about 0.2 degrees, including about 0.1 degrees. The threshold may also or alternatively include or when changes in in the similarity metric GC approach the machine precision (such as an image processing unit 58) for representing floating-point numbers.

If the optimizer in block 280 determines that a threshold has not been reached then a NO path 282 may be followed to the forward projection block 250. The forward projection may then be altered, such as determining a forward projection at a different perspective relative to the known component in block 226 to form a new forward projection for comparison to the acquired projections from block 220. If the optimizer block 280 determines at a convergence has been achieved (e.g. a difference from a present GC is within a threshold relative to a prior GC) then the converged or optimized transform may be output with the YES path 284.

Appropriate optimization techniques may be used in the optimizer block 280, such as those that may be executed by the processing unit 58, or other appropriate processing unit. In various embodiments, a covariance matrix adaptation evolution strategy may be used to achieve the optimization. The selected strategy may include a stochastic derivative free optimization method. It is understood, however, that other appropriate optimization methods or techniques may be used in the optimizer block 280.

Once the Yes path 284 is followed to output the optimized transformation, the optimized transformation ($\hat{T}$) may be used for modifying the projections acquired in block 220. Modification to the projections acquired in block 220 may be made according to any appropriate process, including those discussed further herein. In various embodiments, inpainting in a selected manner may be performed in a modification block 310, as discussed further herein. Inpainting may include generally known digital inpainting such as an interpolation based inpainting of the acquired projections. During interpolation based inpainting, the pixels or voxels identified as a part of the component or object (e.g. the pedicle screw 120) may be replaced with pixels or voxels of a selected type or manner. For example, the identified pixels, based upon the above described process 200, may be replaced with a selected model or graphical representation of the object (e.g. the pedicle screw 120). In addition or alternatively, the identified pixels or voxels may be replaced with a selected color or feature in the acquired projections that have been identified as the object. In addition to the direct inpainting from a selected model, interpolation may be made determined or identified or replace pixels that are at edges or between identified object pixels or voxels or non-identified pixels or voxels. Moreover, a selected amount of noise, such as an optional random noise component, may be added to the inpainted voxels or pixels to selectively characterize the representation of the object in the projections.

In addition to a direct and/or interpolation based inpainting, various other processes may be used to assist in or preform inpainting. For example, a machine learning process or system may be used to perform the inpainting into the projections. For example, the pixels or voxels identified in the process 200 may be inpainted based upon prior training of a machine learning system. For example, a neural network (e.g. a deep learning system) may be used to determine pixels or voxels to be inpainted based upon training of previously determined object projections and the identification of the object on the projection and the inpainting therein. In various embodiments, therefore, inpainting may replace voxels or pixels in a projection according to an appropriate system such as an interpolation or machine learning base system.

The modification of the projections in block 310 may also include determining or estimated pixel values, such as calculating or computing pixel or voxel values using a selected modeling of an imaging system, such as of the x-ray beam. As discussed above the x-ray beam may include x-rays that are emitted by the emitter 26. The x-rays in an emitted beam may be polyenergetic, such as including a spectrum. Accordingly, the x-rays emitted may not be of only a single frequency or power. The polyenergetic x-ray beam may interact with material in a known manner based upon the polyenergetic identity of the x-ray beam. The interactions may be known based upon the known components, as discussed above, of the various x-ray components (defined by the x-ray spectrum) with the object in the projections. Accordingly, the determined pixel values based upon the known polyenergetic model of the x-ray beam may be used to generate pixel or voxel values in the projections and therefore may be used to replace the determined pixels in the projections.

As discussed above, the projections may be modified in various manners and in appropriate processes. Discussion herein to inpainting is merely exemplary, and not intended to limit the scope of the subject disclosure of the following claims. Accordingly, modifying may include inpainting in the projections acquired in block 220 at modifying (e.g. inpainting) block 310. The inpainting block 310 is the first process or step of the reconstruction process 290. The reconstruction process 290 may also be referred to as a metal artifact reduction or removal (MAR) process. Accordingly, the MAR reconstruction may be used to reduce or remove artifacts due to the selected item, such as the pedicle screw 120. By reducing the metal artifacts, or other selected artifacts, in the inpainting block 310, the artifacts are removed for the later reconstruction. Reconstruction may include or be based on a back projection reconstruction including a filtered back projection (FBP). In various embodiments, the back projection may be a three-dimensional (3D) projection in block 320. A reconstruction occurs in block 330 which may form the reconstruction of the image 64 for viewing on the display device 66.

With continuing reference to FIG. 4 and FIG. 5, inpainting block 310 uses the optimized transformation to inpaint the acquired projections from block 220. As illustrated in process 200, the projections (p) are input with the optimized transformation or converged transformation $\hat{T}$ into inpainting block 310. In the inpainting block 310, the surrounding pixels of projections (p) may be used to interpolate the region identified by the forward projection of the KC. Alternatively, the DRR of the forward projection ($\hat{p}$) that accounts for the various effects of x-ray and metal interaction may be painted into the acquired projection 220 at the registered position based on the optimized transform $\hat{T}$ from the optimizer block 280. In other words, selected polyenergetic signal models informed by the KC model of the component shape and material content, based on known material interactions with X-rays included in the forward projection, may be used to paint into the acquired projection 220 at the registered position. Accordingly, the pixels in the acquired projections 220 that match or have the greatest similarity metric to the forward projection from block 250 are replaced with the forward projection from block 250 in the inpainting block 310.

As noted above, with reference to FIG. 5, the projection from block 220, or one of the projections, includes the vertebrae 124p and the imaged screw 120p. Once the transformation is optimized in block 280 the forward projection that is optimized or best matches the screw 120p in FIG. 5 part (b) may be replaced or inpainted with the forward projection from block 250. As illustrated in FIG. 5 part (e), an inpainted screw 120ip (schematically illustrated by a dotted line in part (f)) may be inpainted or used to replace the screw 120p in the projection and replace it in the image, including the vertebrae 124p. As discussed above the acquired projections in block 220 may include one or more of the projections acquired of the subject 14. In various embodiments the number of projections may include three projections, six projections, all of the projections, or any appropriate number. In various embodiments, the acquired projections in block 220 may include six projections that are offset or displaced from one another by 30 degrees (or any appropriate selected angle theta ($\theta$) around the subject 14. The similarity metric in block 270 and the optimized transformation in block 280 may be for only a portion or selected number of the projections of the subject 14. However, it is understood, that the use of the known component parameters in block 226 may minimize or allow for a fast and efficient registration based upon a forward projection in block 250 that similarly or most closely matches the actual projections in block 220 due to the known component parameters in block 226. THE KC parameters, again, may include size, shape, material, and interaction with X-rays. Nevertheless the inpainting in block 310 may replace the identified screw 120p with the inpainted forward projection that has been registered thereto as discussed above. The projection may then become an inpainted projection, such that the inpainted projection in FIG. 5 part (e), in block 310 including the inpainted selected portion or item.

The inpainting in block 310 may also include various optimization or robustness features. For example, the forward projection from block 250, which may also be referred to as a mask, may be dilated or expanded relative to the exact, known component parameters from block 226 relative to the projections from block 220. In various embodiments, the forward projection mask from block 250 may have a dilation or be dilated one or more pixels when inpainting on the projection in block 310. The dilation may assist in overcoming errors such as manufacturing variation, geometric calibration of the imaging system, floating precision errors, or other possible errors. The selected amount of dilation or expansion of the mask assists in ensuring appropriate positioning or accounting for errors, as noted above. The final reconstruction, as discussed herein, which may be the image 64 would include the dimensions of the KC parameters from block 220 to illustrate the extent or placed (implanted) final position of the pedicle screw 120 in the vertebrae 124.

Further, the optimized transformation from block 280 identifies the selected item in the projection to be inpainted in block 310. The inpainting process or method may be selected from appropriate methods. For example, inpainting may include a linear interpolation in the selected projection. In various embodiments, the linear interpolation is achieved by producing a Delaunay triangulation over a convex hull of the regions (e.g. Quickhull algorithm disclosed in Barber, C. B., Dobkin, D. P., and Huhdanpaa, H. T., "The Quickhull algorithm for convex hulls," ACM Trans. on Mathematical Software, 22(4):469-483, 1996) masked (such as with the DRR of the forward projection 260) by the identified transformation from block 280 followed by a barycentric interpolation on each produced triangle. The inpainting process (including in various embodiments, at least one of the interpolation-based or the model-based that exercises the KC model) is then repeated for all of the projections (such as all of the projections acquired in block 220) and measurements in each of the projections input in block 220.

Once the modification in block 310, such as including inpainting in the projections from block 220, is completed, a reconstruction may be performed in block 320 with the modified projections. The reconstruction may be any appropriate reconstruction, as discussed herein. The reconstruction may be used for various purposes as discussed herein.

In various embodiments, the reconstruction in block 320 may include a three-dimensional filtered back projection (3D FBP). In exemplary embodiments, the 3D FBP may include the Feldkamp-Davis-Kress algorithm reconstruction method generally known in the art. It is understood, however, that other appropriate reconstruction (e.g. alternative back projection) methods may be used.

In addition to and/or alternative to the filtered back projection, an iterative reconstruction may also be performed. The iterative reconstruction may include a model based iterative reconstruction (MBIR) algorithm. The iterative reconstruction may include iteratively altering parameters of a model to achieve or minimize a difference between the model and the modified projections from block 310. For example, a model of the object, such as the pedicle screw 120, may be identified and a projection through the model may be iteratively altered to match the modified projections from block 310. When a match is achieved, the model may be used to assist in the reconstruction of the model projections.

Based upon the back projections from block 320, the reconstruction process 290 may output the reconstructed image in block 330. The reconstructed image may be a visualization of the reconstruction. The visualization may be displayed as an image for viewing, such as displayed as an image with the display device 66.

The outputted reconstruction in block 330 may be referred to as a KC-MAR reconstruction and/or a visualization (e.g. a KC-MAR reconstruction visualization). The output, including the visualization, may include or be represented as the image 64 for display on the display device 66 for viewing by the user 54. The reconstruction may include a three-dimensional reconstruction and/or may illustrate the back projections as images for viewing by the user. With reference to FIG. 6 a back projection of uncorrected acquired projections in block 220 is illustrated in row A. A reconstruction using the process 200, including the KC registration 240 and the reconstruction process 290, is illustrated in row B. As clearly illustrated in FIG. 6, row B, having the inpainted registered known components, reduces metal artifacts or selected distortion. The distortion reduction allows for viewing or reconstruction visualization that includes sharper or higher contrast edges with reduced or minimal streaking and other artifacts in the reconstruction.

As illustrated in FIG. 6 row B, the reconstruction visualization may also include selected information based upon the know components from block 226. As discussed above, the inpainting in block 310 may be inpainted with the mask from the forward projection in block 250. The forward projection in block 250 includes the known components parameters from block 226. Accordingly, the inpainting may include various geometric configurations, such as size, shape, and configuration, and the mask of the forward projection from block 250 may also include differentiation of materials due to different attenuation due to different materials of the known components. For example, as discussed above, the head 120" of the pedicle screw 120 may be a different material or formed of a different material than the shank 120'. Accordingly, the reconstruction in FIG. 6 row B may differentiate, such as due to grayscale, the reconstructed portions of different materials. In various embodiments, therefore, the reconstructed projection of the head 120"r may have a different or altered greyscale or visual effect from the shank 120'r. This is due, at least in part, to the forward projection from block 250 being based upon the known component parameter. The KC parameters in block 226 may be exhaustive regarding the known component, such as the pedicle screw 120.

As the known component parameters may include size and geometry and also include materials, the effects of each may be known and applied for forming the forward projection and the inpainting in block 310. Again, as discussed above, the known components and their effects on the X-ray projections may be predetermined and known and saved and recalled for the forward projection in block 250 and the inpainting in block 310. The back projection reconstruction in block 320 and a reconstruction visualization or output in block 330, respectively, may therefore also be based upon the known component parameters from block 226.

The reconstruction visualization, or the visualization in block 330, may be generated in various formats and/or selected by a user from one or more options. The visualization may include a direct reconstruction of the modified projection from block 310. For example, the reconstruction from block 320 may be displayed for viewing by the user 54. The reconstruction, as discussed above, may include incorporating the modified projections directly into a reconstruction projection. The plurality of projections or a selected plurality of projections may be used to generate a three-dimensional (3D) model or visualization for viewing by the user 54. Accordingly, the visualization in block 330 may be a direct visualization or visualization of the direct reconstruction from block 320.

In various embodiments, the visualization may also include and/or alternatively include picture or image elements (e.g. voxels or pixels) that coincide with a registered object in the modified projections from block 310. For example, once the object is registered, as discussed above, the projection may have the pixels or voxels that coincide or are registered as the object is replaced with a selected other pixels or voxels. For example, selected color, gradient, or type of pixel or voxel may be used to replace the registered voxel in the visualization in block 330. Accordingly, an additional or alternative visualization may not be required or generated, just that the pixel or voxels related to the registered object may be replaced.

As a further alternative and/or additional visualization, selected slices or 2D portions may be displayed relative to a selected feature or parameter of the object. For example, once the object has been identified or registered in the projections (e.g. the pedicle screw 120) slices that include the object and/or coincide with the object may be oriented or re-oriented and illustrated in a selected manner, such as along a long axis of the object. For example, as illustrated in FIG. 6, the illustration or visualization for display may be oriented such that a long axis 102L of the screw 120 is used to orient the visualization. Therefore, the long axis 102L may be used to orient the images vertically and if a plurality of slices or 2D images are displayed they may all be displayed substantially in parallel.

As a further alternative and/or addition, a graphical representation may be superimposed or overlaid on the selected image. For example, as discussed above, the object may include the pedicle screw 120. Further, the object may be determined and/or identified based upon known components, which may include a model of the object. Accordingly, a selected portion or version of the object (such as a representation or outline thereof) may be displayed relative to the image. In various embodiments, for example, the graphical representation may be overlaid or superimposed on the image at the registered location of the object.

Accordingly, the visualization in block 330 may include any appropriate visualization. The visualization may be based upon the registered or known position of the object, such as the pedicle screw 120, in the acquired projections. The visualization may then be displayed on the display device 66, such as the image 54, for viewing by the user 54 for various purposes. In various embodiments, therefore, the little artifacts may be reduced in the visualization block 330 such that the user 54 may view the visualization 64 on the display device 66 with substantially reduced and/or eliminated distortions or artifacts due to metaled or other component in the image.

In light of the above, the final reconstruction and/or reconstruction visualization in block 330, which may be displayed as the image 64 on the display device 66, may have substantially reduced or eliminated artifacts due to altered attenuation or distorted attenuation of the X-rays from the imaging system 12 for imaging of the subject 14.

Moreover, the known component parameters 226 may assist in enhancing a registration in block 280, such as making it faster by efficiently and more definitely defining the component for forming the forward projection in 250. Moreover, the known component parameters from block 226 may further assist in reducing artifacts and distortion due to a predetermined and know effects of the component for the inpainting in block 310. Thus, the final reconstructed image in block 330 is efficiently and quickly produced based upon the process 200 that may be executed with the processing system, such as the image processing unit 58 as discussed above.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method of reducing artifacts in an image due to an object, comprising:
   accessing parameters of the object;
   creating at least one forward projection of the object based on the accessed parameters;
   registering the object in the forward projection to at least one acquired projection having the object therein;
   modifying the at least one acquired projection to a representation of the registered object; and generating a reconstruction based on the modified at least one acquired projection.

2. The method of claim 1, wherein modifying the at least one acquired projection includes inpainting the representation of the object in the at least one acquired projection.

3. The method of claim 1, further comprising:
acquiring a plurality of the projections;
modifying at least a first sub-plurality of acquired projections of the acquired plurality of projections to the representation of the registered object;
wherein generating the reconstruction includes generating the reconstruction based on all of at least the first sub-plurality of acquired projections of the acquired plurality of projections.

4. The method of claim 3, wherein generating the reconstruction based on at least all of the modified first sub-plurality of acquired projections of the acquired plurality of projections includes generating a three dimensional image.

5. The method of claim 4, further comprising:
generating a visualization of the reconstruction for display with a display device.

6. The method of claim 5, wherein generating the visualization comprises at least one of:
generating a direct reconstruction of modified projection values of the modified first sub-plurality of acquired projections;
replacing voxels or pixels that coincide with the registered object in the modified first sub-plurality of acquired projections;
orienting the visualization such that a 2D slice coincides with at least one feature of the object;
superimposing a graphical representation of the object on a display of the at least one of the projections of the acquired plurality of projections; or
combinations thereof.

7. The method of claim 4, wherein the generated reconstruction is based on at least one of a filtered back projection, a model-based iterative reconstruction process, or combinations thereof.

8. The method of claim 1, further comprising:
determining the parameters of the object to include at least one of a geometry, number of portions, dimensions, materials, interaction of X-rays with the materials, degrees of freedom in motion of the object, or combinations thereof.

9. The method of claim 8, wherein creating the forward projection of the object based on the accessed parameters includes creating a digitally reconstructed radiograph of the object.

10. The method of claim 8, wherein the determined parameters are comprised of at least one of exact values based on specifications of the object, parametrically defined, or combinations thereof.

11. The method of claim 10, wherein the parametrically defined parameters of the object are determined during the registering the object in the forward projection to at least one acquired projection having the object therein.

12. The method of claim 1, further comprising:
placing the object in a subject; and
acquiring the at least one projection of the subject and the placed object.

13. The method of claim 1, wherein modifying the acquired projections according to the representation comprises at least one of:
an interpolation-based inpainting of the acquired projections;
machine-learning based inpainting using prior training; or
determining estimated pixel or voxel values using poly-energetic modeling of x-rays in an x-ray beam.

14. The method of claim 1, further comprising:
generating a visualization based on the generated reconstruction with reduced artifacts in the generated visualization due to the objects in the at least one acquired projection based on the modified at least one acquired projection.

15. A system for reducing artifacts in an image due to an object, comprising:
a processor system configured to execute instructions for:
accessing parameters of the object;
creating at least one forward projection of the object based on the accessed parameters;
registering the object in the forward projection to at least one acquired projection having the object therein;
modifying the at least one acquired projection to a representation of the registered object; and
generating a reconstruction based on the modified at least one acquired projection; and
a display device to display a visualization based on the generated reconstruction.

16. The system of claim 15, wherein the processor system is further configured for:
accessing a plurality of the projections; and
modifying at least a first sub-plurality of acquired projections of the acquired plurality of projections to the representation of the registered object;
wherein generating the reconstruction includes generating the reconstruction based on all of at least the first sub-plurality of acquired projections of the acquired plurality of projections.

17. The system of claim 16, wherein generating the reconstruction based on at least all of the modified first sub-plurality of acquired projections of the acquired plurality of projections includes generating a three dimensional image.

18. The system of claim 17, wherein the processor system is further configured for:
generating the visualization for display with the display device comprising at least one of:
generating a direct reconstruction of modified projection values of the modified first sub-plurality of acquired projections;
replacing voxels that coincide with the registered object in the modified first sub-plurality of acquired projections; or
orienting the visualization such that a 2D slice coincides with at least one feature of the object;
superimposing a graphical representation of the object on a display of the at least one of the projections of the acquired plurality of projections; or
combinations thereof.

19. The system of claim 15, wherein the processor system is further configured for:
determining the parameters of the object to include at least one of a geometry, number of portions, dimensions, materials, interaction of X-rays with the materials, degrees of freedom in motion of the object, or combinations thereof.

20. A method of reducing artifacts in an image due to an object, comprising:
operating a processor system for:
accessing parameters of the object;
creating at least one forward projection of the object based on the accessed parameters;

registering the object in the forward projection to at least one acquired projection having the object therein;
modifying the at least one acquired projection to a representation of the registered object; and
generating a reconstruction based on the modified at least one acquired projection;
displaying a visualization of the generated reconstruction.

\* \* \* \* \*

UNITED STATES PATENT AND TRADEMARK OFFICE
CERTIFICATE OF CORRECTION

PATENT NO. : 11,756,242 B2
APPLICATION NO. : 17/493208
DATED : September 12, 2023
INVENTOR(S) : Patrick A. Helm et al.

It is certified that error appears in the above-identified patent and that said Letters Patent is hereby corrected as shown below:

In the Specification

Column 3, Detailed Description, Line 29, Delete "28" and insert --26-- therefor

Column 3, Detailed Description, Line 44, Delete "28" and insert --26-- therefor

Column 5, Detailed Description, Line 3, After "STEALTHSTATION®", insert --,--

Column 5, Detailed Description, Line 3, Before "TREON®,", insert --TRIA®,--

Column 13, Detailed Description, Line 35, Delete "K." and insert --κ.-- therefor Column 13, Detailed Description, Lines 39-40, Delete "$\hat{p}(\kappa,T)=\int_{\vec{r}}\kappa(T)d\vec{r}^2$," and insert --$\hat{p}(\kappa,T) = \int_{\vec{r}} \kappa(T)d\vec{r}$-- therefor Column 14, Detailed Description, Line 18, Delete "p," and insert --$\hat{p}$,-- therefor Column 14, Detailed Description, Line 46, Delete "in in" and insert --in-- therefor Column 14, Detailed Description, Line 60, After "transform", insert --$\hat{T}$--

Column 19, Detailed Description, Line 55, Delete "54," and insert --64,-- therefor Signed and Sealed this
Sixteenth Day of April, 2024

Katherine Kelly Vidal
*Director of the United States Patent and Trademark Office*